United States Patent
Grossinger et al.

(10) Patent No.: US 7,110,117 B2
(45) Date of Patent: Sep. 19, 2006

(54) HAIR COLOR MEASUREMENT AND TREATMENT

(75) Inventors: Israel Grossinger, Rehovot (IL); Avigdor Schertz, Rechovot (IL); Michel Mercier, Herzilia (IL); Eli Benny, Rishon Lezion (IL)

(73) Assignee: SeeThrough Ltd., Nes Ziona (IL)

( * ) Notice: Subject to any disclaimer, the term of this patent is extended or adjusted under 35 U.S.C. 154(b) by 211 days.

(21) Appl. No.: 10/345,249

(22) Filed: Jan. 16, 2003

(65) Prior Publication Data

US 2004/0000015 A1  Jan. 1, 2004

Related U.S. Application Data

(60) Provisional application No. 60/392,055, filed on Jun. 28, 2002.

(51) Int. Cl.
*G01J 3/46* (2006.01)

(52) U.S. Cl. .................................................... 356/402

(58) Field of Classification Search ............... 356/402, 356/300
See application file for complete search history.

(56) References Cited

U.S. PATENT DOCUMENTS

| | | | |
|---|---|---|---|
| 3,736,064 A | 5/1973 | Kent et al. | |
| 4,434,467 A | 2/1984 | Scott | |
| 5,006,331 A | 4/1991 | Gaskin | |
| 5,384,116 A | 1/1995 | Pawelek et al. | |
| 5,609,484 A | 3/1997 | Hawiuk | |
| 5,744,125 A | 4/1998 | Pawelek et al. | |
| 6,067,504 A | 5/2000 | MacFarlane et al. | |
| 6,157,445 A | 12/2000 | Macfarlane et al. | |
| 6,308,088 B1 | 10/2001 | MacFarlane et al. | |
| 6,314,372 B1 | 11/2001 | Macfarlane et al. | |
| 6,330,341 B1 | 12/2001 | Macfarlane et al. | |
| 6,437,863 B1 | 8/2002 | Macfarlane et al. | |
| 6,452,118 B1 | 9/2002 | van Pinxteren et al. | |
| 6,810,130 B1 * | 10/2004 | Aubert et al. ............... | 382/100 |
| 2002/0010556 A1 | 1/2002 | Marapane et al. | |
| 2005/0036677 A1 * | 2/2005 | Ladjevardi ................. | 382/162 |

FOREIGN PATENT DOCUMENTS

| | | |
|---|---|---|
| JP | 2002322035 | 11/2002 |
| WO | WO01/87245 | 11/2001 |

* cited by examiner

*Primary Examiner*—Gregory J. Toatley, Jr.
*Assistant Examiner*—Kara Geisel

(57) ABSTRACT

A method to change the color of hair. The method includes measuring an initial reflectance spectrum of a sample of the hair and analyzing a contribution of a plurality of natural hair factors to the initial reflectance spectrum. The method also includes calculating a hair treatment based on another reflectance spectrum. A system to measure a reflectance spectrum of a sample includes an integrating sphere having a sampling port and an inner surface and a window disposed near to the sampling port. The window is configured for being placed in close contact with the sample. The system also includes a light source configured to project light onto the sample via the window and a light detector configured to analyze light reflected from the inner surface to produce the reflectance spectrum of the sample.

19 Claims, 11 Drawing Sheets

US 7,110,117 B2

HAIR COLOR MEASUREMENT AND TREATMENT

This application claims priority from U.S. Provisional Application No. 60/392,055 filed Jun. 28, 2002.

FIELD AND BACKGROUND OF THE INVENTION

The present invention relates to a hair treatment and, in particular, it concerns an apparatus to measure a hair reflectance spectrum and a method to determine an appropriate hair treatment based directly upon a hair reflectance spectrum.

By way of introduction, each strand of hair consists of three layers, namely, the medulla, cortex and cuticle. The medulla is the innermost layer of the hair and is composed of a softer keratin-rich material and its occurrence in human hair appears to be variable, usually being present in large thick hairs. The cuticle is the outermost surface of the hair shaft and is composed of a very hard keratinous substance. It consists of flattened platelets of amorphous keratin, wrapped around the hair shaft in several layers, each layer overlapping the adjacent one, progressing from the root to the tip of the hair. Lastly, the cortex is the inner bulk of the hair, which forms the main body of the hair. The cortex is disposed between the medulla and the cuticle. It is composed of a much softer, fibrous, crystalline keratin. It provides strength, color and texture to the hair. Human hair gets its colors from specialized cells in the hair follicle called melanocytes that produce the pigment for hair. Humans normally produce two type of melanin, namely, Eumelanin and Pheomelanin. Eumelanin is associated with a dark brown color and Pheomelanin is associated with an orange color. Brown and black hair is given its color primarily by Eumelanin. Red hair is given its color primarily by Pheomelanin. Blond hair and hair that has gone white with age have very few of either pigment.

A hair treatment to change an initial hair color to a final hair color normally involves bleaching and/or dyeing. The hair may need to be bleached to reduce the natural Eumelanin and Pheomelanin pigments. The extent of the bleaching depends upon the initial and final hair color. A diluted solution of hydrogen peroxide is generally used as the bleaching agent. The oxygen in the diluted solution of hydrogen peroxide opens up the cuticle of the hair so that the bleaching agent can enter into the cortex to remove the Eumelanin and Pheomelanin pigments. Once bleaching is complete, the hair dye is applied to the hair, if necessary. The hair dye also includes oxygen, which opens up the cuticle of the hair so that the coloring agent can enter into the cortex.

Therefore, the accuracy of the hair coloring process relies upon the skill of the hairdresser to determine how much bleaching is required and which hair dye or combination of hair dyes should be applied to provide the customer with the desired final color. Part of the hairdresser's skill is based upon accumulated experience as well as guidelines issued by the dye manufacturer. However, the final color is often a matter of surprise to both the hairdresser and the customer.

Of relevance to the present invention is U.S. Pat. No. 4,434,467 to Scott. The patent to Scott describes a method whereby the customer chooses a color from a database that is the closest match to his or her own hair color. The customer then chooses a desired final color from the database. The computer then suggests a treatment based on the manufacturer instructions. A shortcoming of the aforementioned system is that the customer has to determine by visual comparison, the closest match to his or her own hair color. A further shortcoming of the aforementioned system is that the system is limited to hair treatments, which are based upon a fixed selection of initial hair colors, thereby not taking into account the individual's hair color.

Also of relevance to the present invention is U.S. Pat. No. 5,609,484 to Hawiuk. Hawuik teaches the use of color filament swatches to recreate the initial hair color and then to add color filament swatches, which are related to a known hair dye, to see how the initial hair color is affected by the hair dye. A shortcoming of the aforementioned system is that the system is not accurate. A further shortcoming of the aforementioned system is that determining the initial color involves a high degree of estimation. An additional shortcoming of the aforementioned system is that this system does not address bleaching of the initial hair color.

Of most relevance to the present invention is U.S. Pat. Nos. 6,067,504, 6,157,445, 6,308,088, 6,314,372 and 6,330,341 to MacFarlane, et el. These patents discuss a method, which first includes obtaining a reflectance spectrum from a sample of hair. The coefficients of the Hunter L, a and b color coordinates of the reflectance spectrum of the hair sample are then analyzed by a computer. The initial hair color is then classified by the computer according to a range of coefficients of the color coordinates stored in a lookup table. A user then chooses a desired hair color from a choice of possible final colors. The computer then determines the appropriate hair treatment based upon a hair treatment stored in a lookup table for the initial hair color and the desired final hair color. A shortcoming of the aforementioned system is due to the initial hair color being classified according to an artificial color, which fits into a range of possible colors. Therefore, the suggested hair treatment does not accurately reflect the users initial hair color. A further shortcoming of the aforementioned system is that the creation and maintenance of the hair treatment lookup table requires a vast number of experiments. For example, for each hair dye, experiments are needed for all the possible initial and final hair colors that can be achieved for that dye. Additionally, the use of the L, a, b color coordinate system can be misleading in certain cases. For example, two samples of hair, which look substantially the same to the human eye may have the same L, a, b color coordinate values even though they have different spectrums of reflectance. For example, one natural blond hair sample which is colored with dye A, may have the same color coordinates as another hair sample, say, a brown hair colored with a dye B. Therefore, simply looking at the L, a, b color coordinates may lead to spurious results.

There is therefore a need for a method to determine a hair treatment based directly upon a person's initial hair color.

Additionally, a large sample of hair is typically required to produce a usable reflectance spectrum of hair. Therefore, there is a need for a system and method to produce a usable reflectance spectrum of hair without having to remove the hair from the customer's head.

SUMMARY OF THE INVENTION

The present invention is an apparatus to measure a hair reflectance spectrum and a method to determine an appropriate hair treatment based directly upon a hair reflectance spectrum.

According to the teachings of the present invention there is provided, a method to change the color of hair, comprising the steps of: (a) measuring an initial reflectance spectrum of a sample of the hair; and (b) analyzing a first contribution of a first plurality of factors to the initial reflectance spectrum, wherein at least two of the first factors are natural hair factors.

According to a further feature of the present invention, the first factors include a factor relating to Eumelanin and a factor relating to Pheomelanin.

According to a further feature of the present invention, there is also provided the step of calculating a new reflectance spectrum based on a hypothetical hair treatment.

According to a further feature of the present invention, the step of calculating is iterated until a difference between the new reflectance spectrum and a desired reflectance spectrum is substantially minimized.

According to a further feature of the present invention, there is also provided the step of calculating a hair treatment based on a second reflectance spectrum.

According to a further feature of the present invention, there is also provided the step of determining a change in the first contribution of at least one of the natural hair factors due to bleaching for a specified time period.

According to a further feature of the present invention, there is also provided the step of determining a change in the first contribution of at least one of the natural hair factors due to dyeing.

According to a further feature of the present invention, there is also provided the step of at least one process selected from the group consisting of bleaching the hair and dyeing the hair.

According to the teachings of the present invention there is also provided, a method to change the color of hair, comprising the steps of: (a) measuring an initial reflectance spectrum of a sample of the hair; (b) analyzing a contribution of a plurality of factors to the initial reflectance spectrum; and (c) calculating a new reflectance spectrum based on a hypothetical hair treatment.

According to a further feature of the present invention, the step of calculating is iterated until a difference between the new reflectance spectrum and a desired reflectance spectrum is substantially minimized.

According to a further feature of the present invention, the calculating is performed by steps including summing a new contribution of the factors after the hypothetical hair treatment.

According to a further feature of the present invention, at least two of the factors are natural hair factors.

According to a further feature of the present invention, the factors include a factor relating to Eumelanin and a factor relating to Pheomelanin.

According to a further feature of the present invention, the hypothetical hair treatment includes at least one process selected from the group consisting of bleaching the hair and dyeing the hair.

According to a further feature of the present invention, the dyeing is performed by using a plurality of dyes.

According to a further feature of the present invention, the dyes include natural hair factor dyes.

According to a further feature of the present invention, there is also included the step of at least one process selected from the group consisting of bleaching the hair and dyeing the hair.

According to the teachings of the present invention there is also provided, a method to change the color of hair, comprising the steps of: (a) measuring an initial reflectance spectrum of a hair sample; (b) analyzing a contribution of a plurality of factors to the initial reflectance spectrum; and (c) calculating a hair treatment based on a second reflectance spectrum.

According to a further feature of the present invention, at least two of the factors are natural hair factors.

According to a further feature of the present invention, the factors include a factor relating to Eumelanin and a factor relating to Pheomelanin.

According to a further feature of the present invention, the hair treatment includes at least one of bleaching and dyeing.

According to a further feature of the present invention, the dyeing is performed using a plurality of dyes.

According to a further feature of the present invention, the dyes include natural hair factor dyes.

According to a further feature of the present invention, there is also provided the step of at least one process selected from the group consisting of bleaching the hair and dyeing the hair.

According to the teachings of the present invention there is also provided, a method to create a natural hair factor dye having a factor which is substantially the same as a natural hair factor, comprising the steps of: (a) mixing a plurality of dyes to create a mixed dye; and (b) measuring a reflectance spectrum of the mixed dye, wherein the mixing is performed such that the reflectance spectrum is substantially the same as the natural hair factor.

According to a further feature of the present invention, there is also provided the step of dyeing hair to a natural hair color using the mixed dye.

According to the teachings of the present invention there is also provided, a system to measure a reflectance spectrum of a sample, comprising: (a) a light probing device; (b) a window disposed near to the light probing device, the window being configured for being placed in close contact with the sample; (c) a light source configured to project light onto the sample; and (d) a light detector configured to analyze light reflected from the sample substantially via the light probing device to produce the reflectance spectrum of the sample.

According to a further feature of the present invention, the light probing device is an integrating sphere.

According to the teachings of the present invention there is also provided, a method for measuring a reflectance spectrum of hair, comprising: (a) placing at least part of a measuring device onto attached hair; and (b) measuring a reflectance spectrum of the hair.

According to a further feature of the present invention, the measuring device includes: (a) a light probing device; (b) a window disposed near to the light probing device, the window being configured for being placed in close contact with the hair; (c) a light source configured to project light onto the hair; and (d) a light detector configured to analyze light reflected from the hair substantially via the light probing device to produce the reflectance spectrum of the hair.

According to a further feature of the present invention, the light probing device is an integrating sphere.

BRIEF DESCRIPTION OF THE DRAWINGS

The invention is herein described, by way of example only, with reference to the accompanying drawings, wherein:

FIG. 8b is a detailed flow chart of part of the process shown in FIG. 8a.

DESCRIPTION OF THE PREFERRED EMBODIMENTS

The present invention is an apparatus to measure a hair reflectance spectrum and method of operation thereof as well as a method to determine an appropriate hair treatment based directly upon a hair reflectance spectrum.

The principles and operation of a hair reflectance measuring apparatus and a method to determine an appropriate hair treatment based directly upon a hair reflectance spectrum according to the present invention may be better understood with reference to the drawings and the accompanying description. It will be appreciated by persons skilled in the art that the present invention can also be applied to other applications including dyeing of fabrics and other materials.

Figure 1:
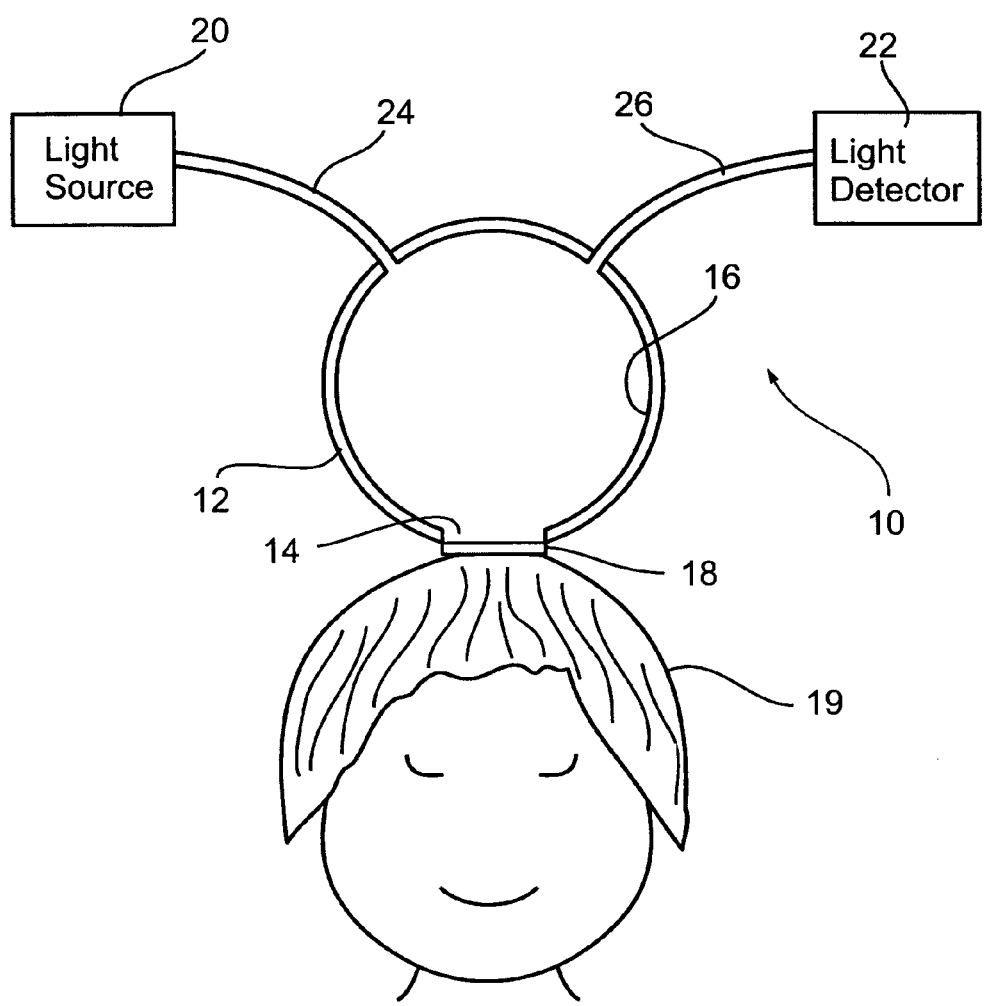
FIG. 1 is a schematic view of a reflectance spectrum measurement system that is constructed and operable in accordance with a preferred embodiment of the present invention.

Reference is now made to FIG. 1, which is a schematic view of a reflectance spectrum measurement system 10 that is constructed and operable in accordance with a preferred embodiment of the invention. Reflectance spectrum measurement system 10 includes a light-probing device, such as an integrating sphere 12 having a sampling port 14 and an inner surface 16. Integrating sphere 12 are commonly used in many optical applications. Inner surface 16 is coated with a substance, which enables inner surface 16 to exhibit very high diffusive reflectance properties, such as Beryllium Sulfate. A transparent window 18 is disposed across sampling port 14 to prevent dirt, contaminants and other foreign substances from entering into integrating sphere 12. Additionally and more importantly, window 18 also enables close contact between integrating sphere 12 and a hair sample 19 by flattening hair sample 19. It is preferable for hair sample 19 to be flat during the measurement of the reflectance spectrum. Reflectance spectrum measurement system 10 also includes a light source 20 and a light detector 22. Light source 20 is connected to integrating sphere 12 via an optical fiber 24. Light source 20 projects light onto hair sample 19 via window 18. Light detector 22 is connected to integrating sphere 12 via an optical fiber 26. Light detector 22 is typically a spectrophotometer. Light detector 22 is configured to analyze light reflected from inner surface 16 to produce a reflectance spectrum of hair sample 19. In use, window 18 of integrating sphere 12 is placed in close contact with attached hair, attached hair being hair which is still attached to the head. Light source 20 projects light onto hair sample 19 via window 18. Light then reflects off of hair sample 19 onto inner surface 16 via window 18. The light then exits integrating sphere 12 via optical fiber 26 to light detector 22. Light detector 22 then produces the reflectance spectrum of hair sample 19. It will be apparent to those skilled in the art that light source 20 and light detector 22 can be arranged in various orientations with respect to integrating sphere 12. It will also be apparent to those skilled in the art that integrating sphere 12 can be substituted by other light probing devices. Before reflectance spectrum measurement system 10 is used to measure a reflectance spectrum, reflectance spectrum measurement system 10 is calibrated by measuring the reflectance spectrum of a white reference material. The white reference material has very high reflectance properties and is typically packaged with integrating sphere 12. Once this calibration measurement has been made, all future reflectance spectra are compared to the reflectance spectrum of the white reference material. Therefore, the typical reflectance spectrum of a sample is displayed as a graph of percentage reflectance (as compared to the white reflectance material) versus wavelength.

By way of introduction, the present invention utilizes natural hair factors, such as Eumelanin, Pheomelanin and other factors which contribute to the reflectance spectra of hair to predict a final hair color based upon a hair treatment or to determine an appropriate hair treatment based upon a desired final hair color.

Figure 2:
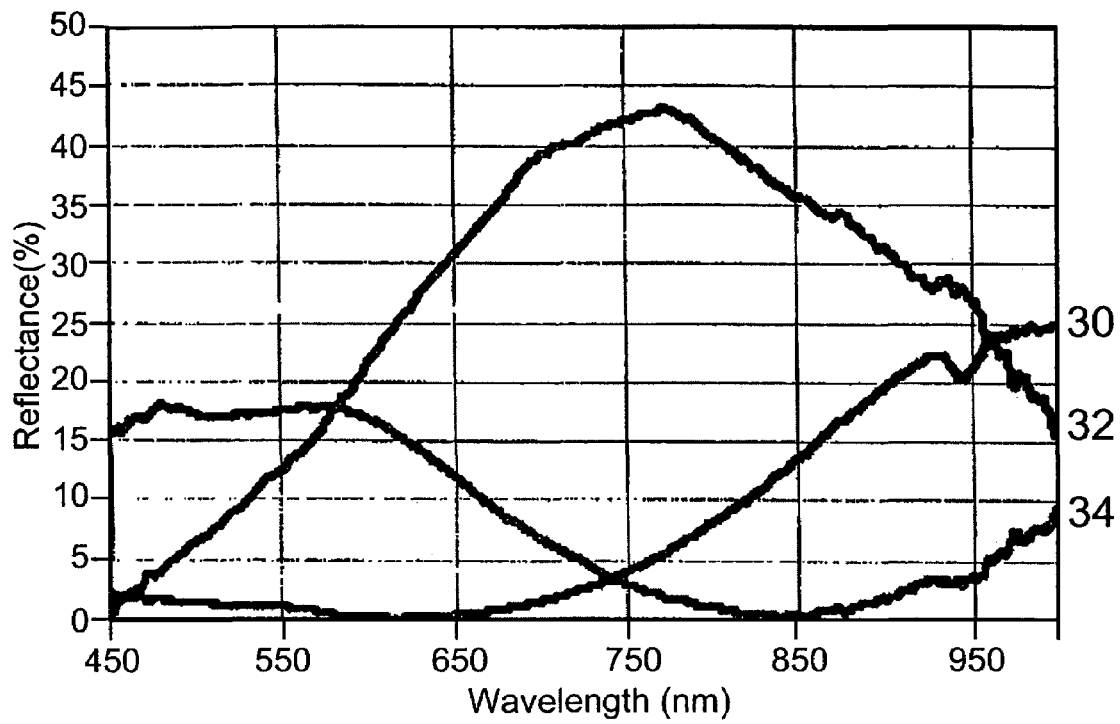
FIG. 2 is a chart showing the reflectance spectra of three factors contributing to the reflectance spectra of natural hair that is operable in accordance with a preferred embodiment of the present invention.
Figure 3:
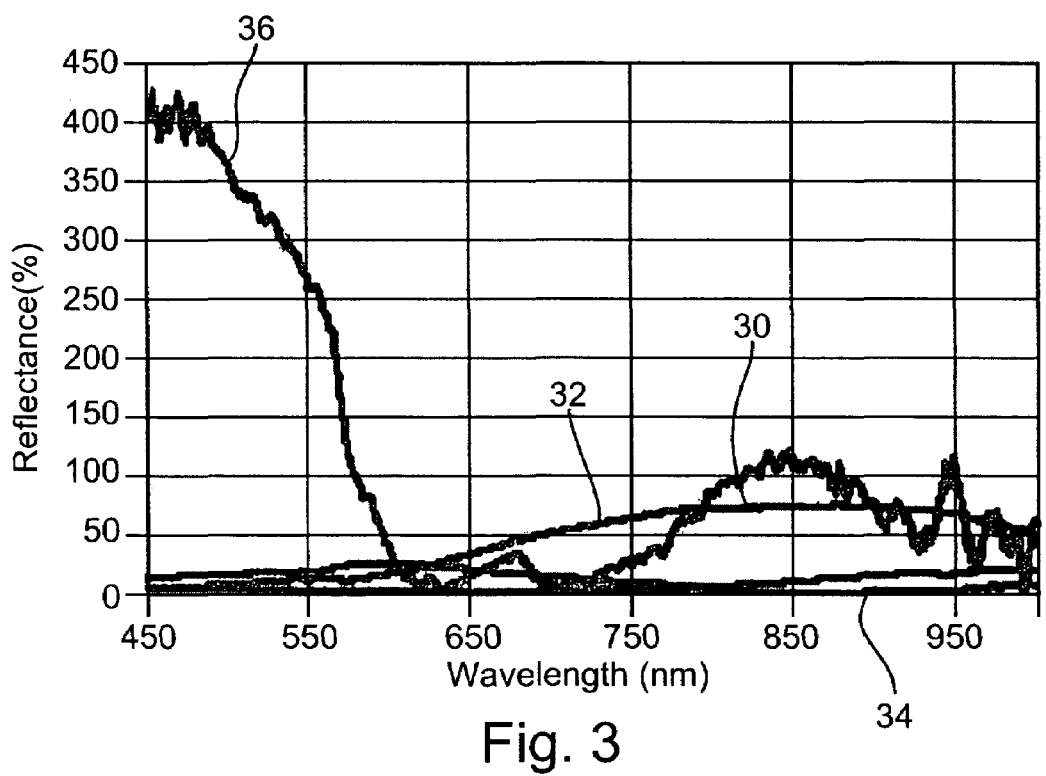
FIG. 3 is a chart showing the reflectance spectra of four factors contributing to the reflectance spectra of natural hair that is operable in accordance with a preferred embodiment of the present invention.

Reference is now made to FIG. 2, which is a chart of percentage reflectance against wavelength in nm showing the reflectance spectra of three factors contributing to the reflectance spectra of natural hair that is operable in accordance with a preferred embodiment of the present invention. The inventors of the present invention measured the reflectance spectra of a large sample of natural hairs and bleached hairs and then performed factor analysis to determine the reflectance spectra of the natural hair factors that contribute to the reflectance spectra of hair. It was also found that bleaching does not add another factor to the reflectance spectrum of hair. Factor analysis is known to one skilled in the art of factor analysis. Additionally, factor analysis is described in the following publications. First, D. Noy, L. Fiedor, G. Hartwich, H. Scheer and A. Scherz (1998) Metal substituted bacteriochlorophylls; 2. Changes in redox potentials and electronic transition energies are dominated by intramolecular electrostatic interactions. J. Am. Chem. Soc. 120, 3684–3693. Second, Noy, R. Yerushalmi, V. Brumfeld, I Ashur, H. Scheer, Kim Baldridg and A. Scherz, (2000) Optical Absorption and Computational Studies of [Ni]-Bacteriochlorophyll-a. New Insight into charge Distribution between Metal and Ligands. J. Amer. Chem. Soc., 122 (16), 3937–3944 Malinowski, E. R. Factor Analysis in Chemistry; 2nd ed.; Wiley: 1991. The inventors initially performed their analysis assuming that the reflectance spectra of hair are due to three factors. The first natural hair factor, shown by curve 30, is due to the Eumelanin pigment in hair. The second natural hair factor, shown by curve 32, is due to the Pheomelanin pigment in hair. The third factor, shown by curve 34, is known as the white factor. The white factor is probably related to the characteristics of the keratin. The above three factors are the three main factors present in natural hair. The coefficients of the factors determine the reflectance spectrum for a particular hair. For example, a person with dark hair has a high coefficient of the Eumelanin factor and a person with red hair has a high coefficient of the Pheomelanin factor. The inventors extended their research assuming that the reflectance spectra of hair are due to four factors as shown in FIG. 3, which is a chart of percentage reflectance against wavelength in nm for four factors. In addition to the Eumelanin factor shown by curve 30 and the Pheomelanin factor shown by curve 32 and the white factor shown by curve 34, there is a fourth factor, shown by curve 36, which seems to relate to a consistent error of the apparatus used to measure the reflectance spectra. It will be appreciated by those skilled in the art that the error factor will depend on the type of apparatus being used. For each type of apparatus, the error factor can be determined using factor analysis. This can be done by assuming that only the error factor changes between apparatuses. Alternatively, all four factors can be recalculated for each type of apparatus. Alternatively, the error factor can be ignored and only three-factor analysis can be employed. The inventors additionally extended their research assuming that the reflectance spectra of hair are due to five factors. The inventors concluded that either three-factor analysis or four-factor analysis gives the best results. Table 1 shows the data points which can be used to recreate the reflectance spectrum for each factor for both three-factor analysis and four-factor analysis.

Figure 4:
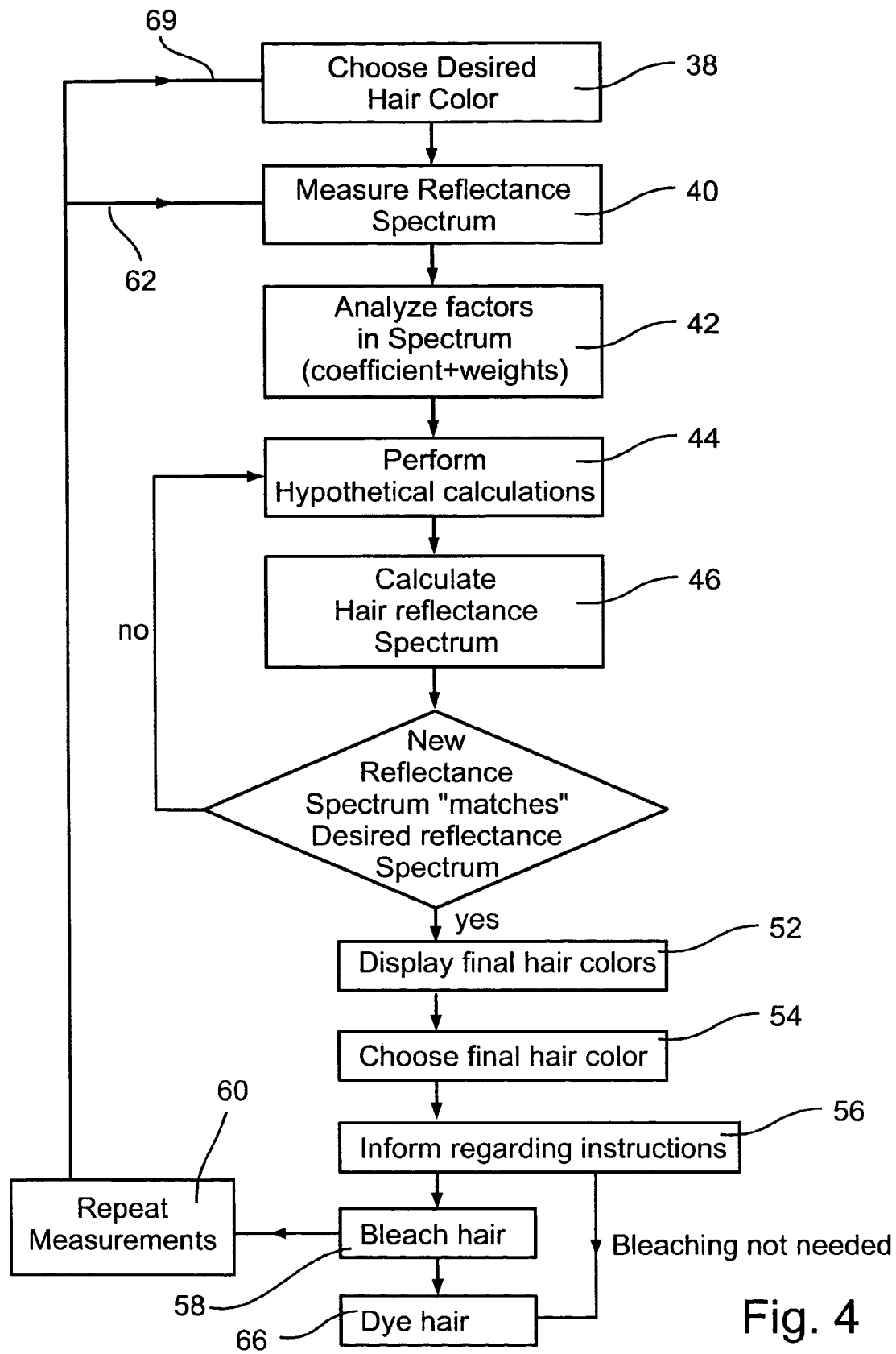
FIG. 4 is a flow chart of the steps involved in changing the color of hair that is operable in accordance with a preferred embodiment of the present invention.

Reference is now made to FIG. 4, which is a flow chart of the steps involved in changing the color of hair in accordance with preferred embodiment of the invention. First, (block 38) a customer chooses a desired hair color from a selection of possible hair colors. The possible hair color selection is typically created by measuring the reflectance spectrum for a large sample of different colored hairs. Each reflectance spectrum is then inputted into a computer. The computer uses the reflectance spectrum to recreate the actual color for displaying on a monitor. The displaying of a color on a monitor based upon a reflectance spectrum is known in the art. It will be apparent to those skilled in the art that the desired colors could be printed on a card or be represented as swatches of dyed hair. Therefore, each of the available colors has a known reflectance spectrum. Second, (block 40) an initial reflectance spectrum of the customer's hair is measured by reflectance spectrum measurement system 10. Third, (block 42) the contribution of the natural hair factors to the initial reflectance spectrum is analyzed by the computer. In other words, the coefficient of each natural factor contributing to the initial reflectance spectrum is determined by the computer, typically using a curve fitting program which performs iterative calculations based on the known natural hair factors and the initial reflectance spectrum. By way of a non-limiting example, instructions that can be used to write a computer program to perform coefficient analysis are given with reference to FIGS. 8a and 8b. Fourth, (block 44) the computer performs hypothetical calculations based upon hypothetical hair treatments to determine a hair treatment which results in a final reflectance spectrum which is as close as possible to the reflectance spectrum of the desired

TABLE 1

Data points for three-factor and four factor analysis

| Wavelength (nm) | 3 factors (% reflectance) | | | 4 factors (% reflectance) | | | |
|---|---|---|---|---|---|---|---|
| | White | Pheomelanin | Eumelanin | Eumelanin | Pheomelanin | White | Error |
| 449.9800 | 15.7104 | 0.7366 | 2.0300 | 0.5784 | 0.8126 | 9.1088 | 410.1482 |
| 467.9900 | 16.9215 | 2.7911 | 1.7620 | 0.4148 | 1.9523 | 10.9837 | 408.6295 |
| 486.8800 | 17.7226 | 5.1005 | 1.5001 | 0.3150 | 3.3559 | 12.7938 | 390.6849 |
| 505.7200 | 17.0110 | 6.9958 | 1.3817 | 0.4194 | 4.8991 | 13.4816 | 339.0551 |
| 524.5200 | 17.2225 | 9.2190 | 1.2118 | 0.4090 | 6.6024 | 14.7920 | 310.5842 |
| 543.2600 | 17.3613 | 11.9606 | 1.0318 | 0.3581 | 9.1140 | 16.0657 | 282.6967 |
| 561.9600 | 17.8852 | 14.0464 | 0.9260 | 0.6002 | 9.6278 | 18.3324 | 231.0784 |
| 580.6100 | 17.8249 | 17.5524 | 0.3855 | 0.9251 | 9.3863 | 22.2275 | 96.7082 |
| 599.2100 | 16.9102 | 21.3338 | 0.2559 | 0.9471 | 13.6714 | 22.9888 | 41.9382 |
| 617.7700 | 15.3779 | 25.0805 | 0.1333 | 0.7795 | 19.1959 | 22.4851 | 6.0427 |
| 636.2800 | 13.5056 | 28.4938 | 0.2671 | 0.5764 | 26.0908 | 20.6223 | 3.3713 |
| 654.7400 | 11.3966 | 31.5082 | 0.5252 | 0.3664 | 33.3505 | 18.0127 | 15.4954 |
| 673.1500 | 9.2616 | 34.5822 | 0.7908 | 0.1546 | 40.7470 | 15.3660 | 28.0484 |
| 691.5100 | 7.4539 | 38.0087 | 1.2874 | 0.3641 | 47.6618 | 13.8990 | 10.9408 |
| 709.8300 | 5.8252 | 39.8407 | 1.9640 | 0.7142 | 52.8616 | 12.0771 | 7.2889 |
| 728.1000 | 4.4744 | 40.7140 | 2.8286 | 1.2097 | 57.0883 | 10.1511 | 15.3769 |
| 746.3200 | 3.0919 | 41.9966 | 3.7709 | 1.7486 | 62.0540 | 8.2156 | 23.9072 |
| 764.4900 | 2.2686 | 42.7094 | 5.0605 | 2.6265 | 66.3255 | 6.7167 | 37.9100 |
| 782.6100 | 1.6167 | 42.6297 | 6.5937 | 3.7073 | 69.9183 | 5.0982 | 59.5171 |
| 800.6900 | 1.0848 | 40.8118 | 8.2845 | 4.9804 | 71.2813 | 3.3011 | 84.1567 |
| 818.7200 | 0.4715 | 38.9247 | 10.0087 | 6.3701 | 72.2323 | 1.7384 | 95.0350 |
| 836.7000 | 0.4071 | 36.8818 | 12.0460 | 8.0518 | 73.0343 | 0.6551 | 111.5327 |
| 854.6300 | 0.3693 | 35.4924 | 14.0776 | 9.8281 | 74.1342 | 0.1440 | 110.3087 |
| 872.5200 | 0.9971 | 33.9771 | 16.5324 | 12.0910 | 74.7387 | 0.5798 | 101.6278 |
| 890.3600 | 1.4347 | 32.3645 | 18.4992 | 13.9346 | 74.6269 | 0.8773 | 91.4167 |
| 908.1500 | 2.3836 | 30.0323 | 20.5567 | 16.1221 | 72.2188 | 2.3930 | 54.4521 |
| 925.8900 | 3.3526 | 27.9514 | 22.2814 | 17.8624 | 70.3974 | 3.4314 | 40.4861 |
| 943.5800 | 3.0357 | 27.8602 | 20.2160 | 15.7161 | 69.2665 | 1.9716 | 94.0455 |
| 961.2300 | 5.1819 | 23.6027 | 23.4799 | 19.3271 | 63.7427 | 5.2953 | 28.1399 |
| 978.8200 | 6.8208 | 20.5698 | 24.1780 | 20.0350 | 59.6380 | 6.1958 | 53.9457 |
| 996.3800 | 9.1525 | 16.1569 | 24.7946 | 21.0241 | 51.6781 | 8.6234 | 47.4904 | color. In this step, the computer calculates the change in the coefficients of each of the natural hair factors due to a hypothetical bleaching time and a hypothetical application of a dye or a combination of dyes. The effect of bleaching on the natural hair factors is described below in more detail with reference to FIGS. 5a, 5b, 5c, 5d and 5e. The effect of dyeing on the natural hair factors using a dye which has a factor which is dissimilar to one of the natural hair factors is described below in more detail with reference to FIG. 6. The effect of dyeing on the natural hair factors using a dye which has a factor which is similar to one of the natural factors is described below in more detail with reference to FIG. 7. Dyes that have a very high correlation with the natural hair factors of Eumelanin and Pheomelanin are described as natural hair factor dyes. Natural hair factor dyes can be used when the desired hair color is a natural hair color. When a dye is introduced, a new factor associated with that dye is typically introduced as well. After the computer calculates the new coefficients of the factors, the computer calculates a new reflectance spectrum (block 46), based on the hypothetical hair treatment, by summing the new contribution of each factor. In other words, the computer calculates a new reflectance spectrum, based on the hypothetical hair treatment, by summing the products of the reflectance spectra of each factor and their associated coefficients. This new reflectance spectrum is then compared with the reflectance spectrum of the desired color (block 48). The computer then performs many iterative calculations until the difference between the new reflectance spectrum and the desired reflectance spectrum is minimized, given the constraints of the iteration process and the available dyes. An exact match is generally not possible due to the constraint of the available dyes. In other words, the computer calculates a hair treatment based on the desired reflectance spectrum given the constraints of the iteration process and the available dyes. It should be noted that if the desired hair color is a natural hair color, then dyeing using synthetic dyes may not be needed, bleaching may be enough. Likewise, if a customer has light colored hair, bleaching may not be necessary to achieve the desired color. Fifth, (block 52) after the computer has completed the iterative calculations, the computer displays the colors of a selected number of possible final hair colors. The possible final hair colors generally include the closest match to the desired hair color as well as several other colors, which are a set gap from the desired color. The set gap can be preset by the hairdresser. Sixth, (block 54) the customer chooses one of the available final hair colors. Seventh, (block 56) the computer informs the hairdresser of the required bleaching time and dyes needed to achieve the chosen color. Eighth, (block 58) if bleaching is required, the hairdresser bleaches the hair for the required time. Ninth, (block 60 optionally at this stage, steps two to seven (line 62), or steps one to seven (line 64), are performed again, before dyeing to achieve more accurate dyeing results. Tenth, (block 66) if dyeing is being performed, the hairdresser dyes the hair using a dye or a combination thereof. It will be apparent to those skilled in the art that other methods using the technology of the present invention are possible. For example, the above steps may be performed in a different order. Also, the customer could be given a number of hair color choices based on the use of a specific dye with differing bleaching times.

Figure 5A:
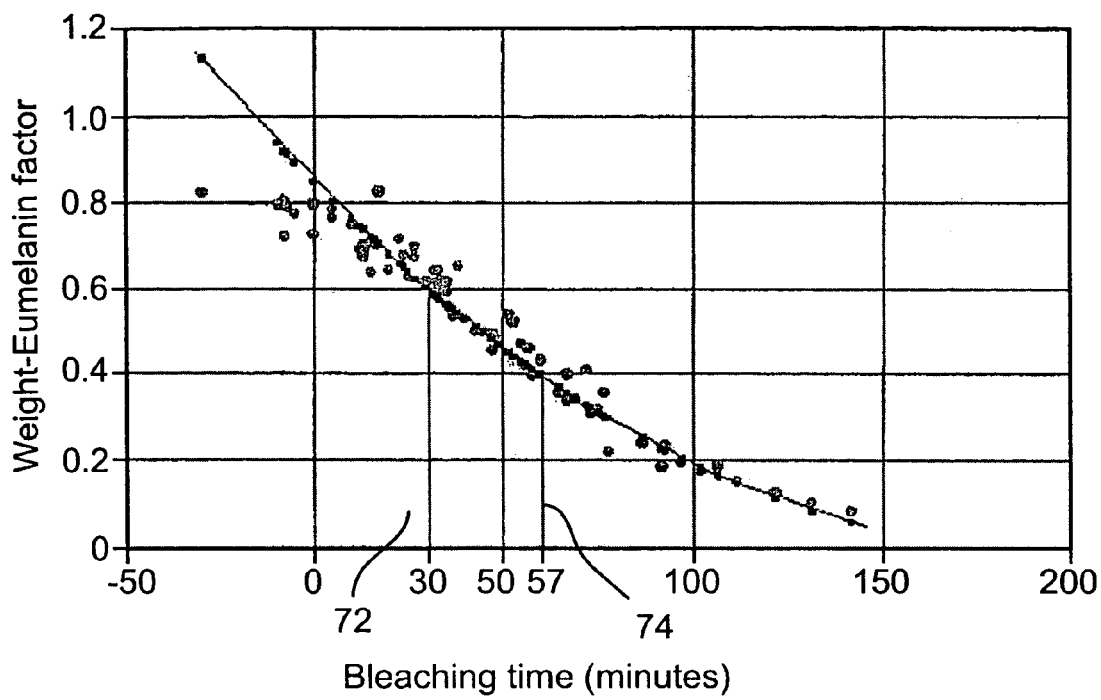
FIG. 5a is a graph showing the weight of Eumelanin against effective bleaching time.

By way of introduction, the inventors have proven by experimentation that the factors of unbleached natural hair are very similar to the factors of bleached hair. Additionally, the inventors have proven that a bright natural hair has substantially the same coefficients of factors as a dark hair that has been bleached to the same color as the bright natural hair. Additionally, the bleaching process is mainly reducing the Eumelanin's concentration within the hair, but the pigments of Pheomelanin are also being removed. Reference is now made to FIG. 5a, which is a graph showing the weight of Eumelanin against effective bleaching time. The following analysis was performed using 4-factor analysis. However, it will be apparent to those skilled in the art that the following analysis can be performed for any number of factors. The weight of Eumelanin is given by the following formula:

$$W_{EU} = \frac{C_{EU}}{C_{EU} + C_{PH} + C_W + C_{ER}},\qquad\text{(Equation 1)}$$

where $W_{EU}$ is the weight of the Eumelanin factor, $C_{EU}$ is the coefficient of the Eumelanin factor, $C_{PH}$ is the coefficient of the Pheomelanin factor, $C_W$ is the coefficient of the white factor and $C_{ER}$ is the coefficient of the error factor. If three-factor analysis is used, the error factor is ignored. Similarly, the weights of the other factors are calculated with respect to the coefficients of all the factors. The graph of FIG. 5a was produced by performing the following steps. A reflectance spectrum of a sample of hair was measured and then $W_{EU}$ was calculated. The sample of hair was then bleached for a specific time. The same sample of hair was then additionally bleached again and $W_{EU}$ was recalculated. The same hair was then re-bleached and $W_{EU}$ was recalculated a number of times. This same process was repeated for a number of hair samples. The bleaching substance used is a mixture of 50% water, 25% Mon-platin Blondy hair bleaching powder and 25% Mon-platin 12% oxygen cream, by weight. The bleaching substance is manufactured by Alef Meshi Industries Ltd., 4 Pinkas David Street, Rishon Le-Zion, Israel. Equations 2 to 6, which are listed below are based on experiments performed with the abovementioned bleaching substance. A new reflectance spectrum was measured and $W_{EU}$ was recalculated. All the sequences were merged into a single graph by supplying the appropriate time-shift for each sequence of dots for each hair sample. For example, a hair sample having an initial weight of the Eumelanin factor 0.6 starts at an effective time of approximately 30 minutes (line 72), another hair sample having an initial weight of the Eumelanin factor of 0.4 starts at an effective time of approximately 57 minutes (line 74). Therefore, by way of example, if a hair sample has an initial $W_{EU}$ of 0.6 and the hair sample is bleached for 70 minutes, the hair sample will have a final $W_{EU}$ of approximately 0.2. This is because the hair sample has an effective start time of 30 minutes and an effective end time of 100 minutes. Additionally, by way of example, if another hair sample has an initial weight of Eumelanin of 0.4, this hair sample has an effective start time of approximately 57 minutes. If this hair sample needs to be bleached to have a weight of Eumelanin of 0.2, which is equivalent to an end time of 100 minutes, then the hair sample needs to be bleached for 43 minutes (100 minutes less 57 minutes). The equation of the graph of FIG. 5a was then calculated using a best-fit method. The equation of the graph of FIG. 5a is:

$$W_{EU}=2.3421\times10^{-5}t_{EU}^{2}-0.0089t_{EU}+0.8455\qquad\text{(Equation 2)},$$

where $t_{EU}$ is the effective bleaching time in minutes for the Eumelanin factor. Equation 2 is valid for any hair sample using the abovementioned bleaching solution. However, it will be appreciated by those skilled in the art, that equation 2 can be recalculated by performing limited experiments using another bleaching substance on a sample of hairs. In order to determine the appropriate equations for another bleaching substance, the samples for used should be from natural unbleached hairs. Hair samples from at least five individuals should be used. Each sample of hair from the same individual should be divided into several smaller samples so that each smaller sample can be bleached for a different duration of time. This procedure is repeated for each individual. All the results are merged together into the same graph by supplying the appropriate time shift to each series of points from each individual. The samples used should be chosen such that, the samples give a large spread over the range of possible natural hair colors (from bright hair to dark hair). The total number of points on the graph should be at least 15. It should be noted that only the constants of equation 2 change with different bleaching substances.

Similarly, the Pheomelanin factor also decreases due to bleaching. However, when a reflectance spectrum is measured and the coefficients of the reflectance spectrum are analyzed, the coefficient and therefore the weight of the Pheomelanin factor only represent the Pheomelanin that is in the background of the Eumelanin. In other words, the dark nature of the Eumelanin pigment prevents a portion of the Pheomelanin factor from contributing to the reflectance spectrum. Therefore, the coefficient and weight of the Pheomelanin factor which are calculated using the analysis of the reflectance spectrum only represent a "background" value. Similarly, the coefficient and weight of the white factor which are calculated using the analysis of the reflectance spectrum only represent a "background" value with respect to the foreground Eumelanin. Therefore, $W_{PH-B}$, which is the weight of the Pheomelanin factor in the background is given by the following equation:

$$W_{PH-B} = \frac{C_{PH}}{C_{PH} + C_W + C_{ER}}. \qquad \text{(Equation 3)}$$

Figure 5B:
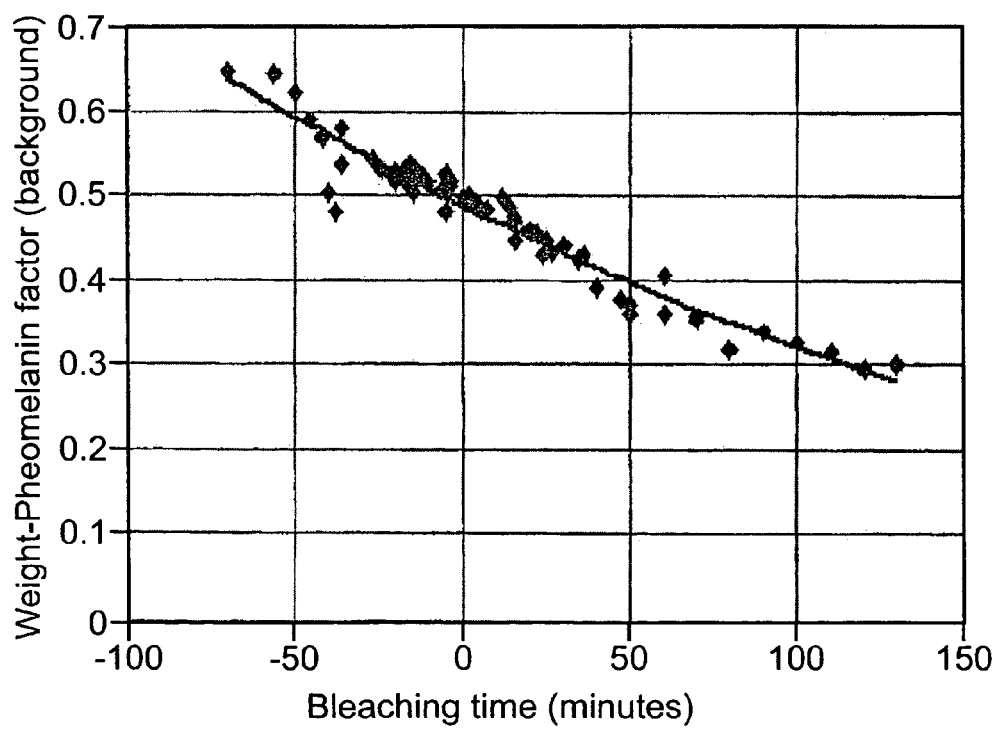
FIG. 5b is a graph showing the weight of the background Pheomelanin factor against effective bleaching time.
Figure 5C:
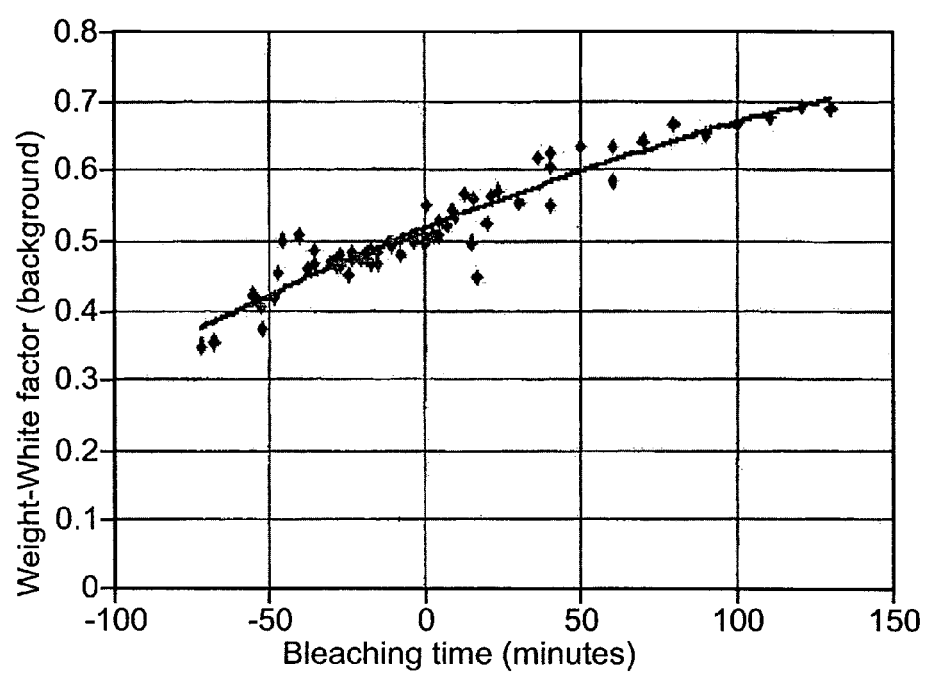
FIG. 5c is a graph showing the weight of the background white factor against effective bleaching time.

The bleaching analysis performed for the Eumelanin factor with reference to FIG. 5a was also performed with respect to the Pheomelanin factor and the white factor. Reference is now made to FIG. 5b, which is a graph showing the weight of the background Pheomelanin factor against effective bleaching time. The equation of the graph of FIG. 5b is then calculated using a best-fit method. The equation of the graph of FIG. 5b is as follows:

$$W_{PH-B} = 3 \times 10^{-6} t_{PH-B}^2 - 0.0019 t_{PH-B} + 0.4883 \qquad \text{(Equation 4),}$$

where $t_{PH-B}$ is the effective bleaching time in minutes of the Pheomelanin factor in the background. It will be appreciated by those skilled in the art, that equation 4 can be recalculated by performing limited experiments using another bleaching substance on a sample of hairs. It should be noted that only the constants of equation 4 change with different bleaching substances. Reference is also made to FIG. 5c, which is a graph showing the weight of the background white factor against effective bleaching time. It is seen from FIG. 5c that the white factor in the background increases with bleaching.

The density of the Pheomelanin factor and the white factor in the Eumelanin foreground is substantially the same as the density of the Pheomelanin factor and the white factor, respectively, in the background. Therefore, the following equation is valid for the Pheomelanin factor:

$$W_{PH}(t) = (1 - W_{EU}(t_{EU})) \times W_{PH-B}(t_{PH-B}) \qquad \text{(Equation 5),}$$

where $W_{PH}(t)$ is the total weight of the Pheomelanin factor as a function of time, $W_{EU}(t_{EU})$ is the total weight of the Eumelanin factor as a function of time and $W_{PH-B}(t_{PH-B})$ is the background weight of the Pheomelanin factor as a function of time.

It should be noted that the error factor does not respond to bleaching. Therefore, it is assumed that this final factor represents the inherent error of the apparatus. Additionally, the final coefficient of the error factor is consistently low. The inventors calculated, using reflectance spectrum measurement system 10, that the final coefficient of the error factor is approximately 0.0036.

Equations 2, 4 and, 5, or their equivalents, are used to calculate the effects of bleaching on the weights of the factors contributing to the reflectance spectrum of a hair sample, as will be explained below with reference to FIG. 5d.

Figure 5D:
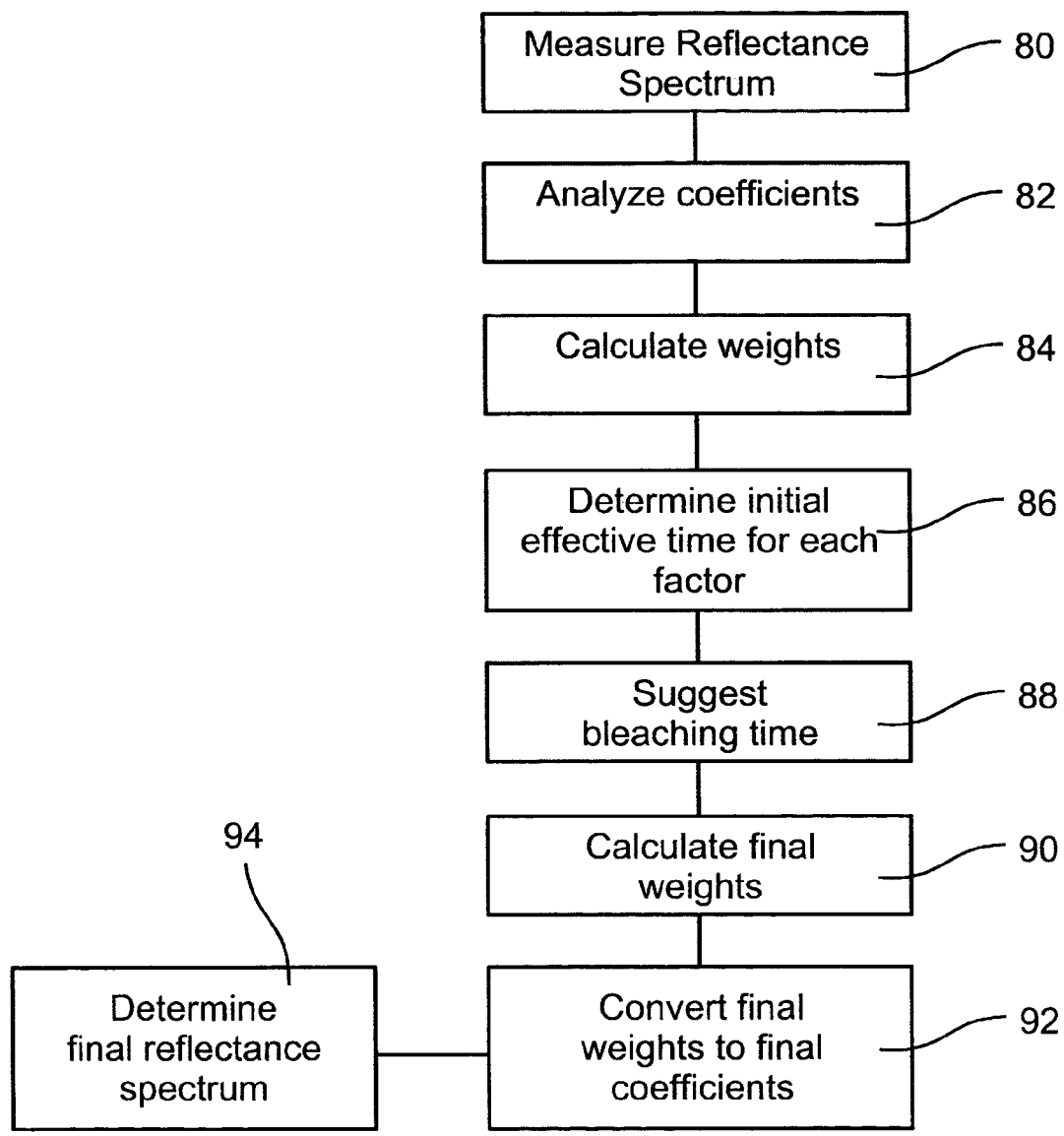
FIG. 5d is a flow chart of the steps involved in determining the effects of bleaching on the reflectance spectrum of hair.

Reference is now made to FIG. 5d, which is a flow chart of the steps involved in determining the effects of bleaching on the reflectance spectrum of hair. First a reflectance spectrum of a sample hair is measured (block 80). Second, the coefficients of the factors are analyzed by the computer (block 82). Third, the weights of the factors are calculated, by the computer, using equation 1 and the equivalents of equation 1 (block 84). For the Eumelanin and the Pheomelanin factors the initial effective time is determined using equations 2 and 4 (block 86). Fourth, the computer suggests a bleaching time (block 88). Fifth, the computer calculates the final weight after bleaching of the Eumelanin factor using equation 2 and the final weight after bleaching of the Pheomelanin factor using equations 4 and 5 (block 90). Sixth, the computer then converts the final weights after bleaching into final coefficients after bleaching (block 92), as will be explained below. At this stage the final coefficient of the white factor is calculated directly from the final weight of the Eumelanin factor, as will be explained below. Seventh, the computer determines a final reflectance spectrum after bleaching by summing the product of each factor with the factor's final coefficient after bleaching (block 94).

Figure 5E:
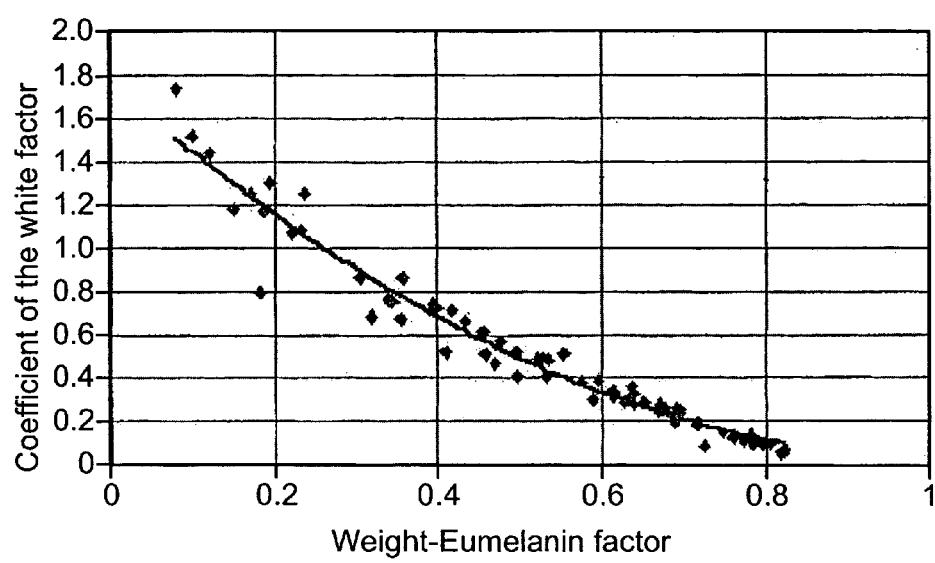
FIG. 5e is a graph showing the coefficient of the white factor against the weight of the Eumelanin factor.

Reference is now made to FIG. 5e, which is a graph showing the coefficient of the white factor against the weight of the Eumelanin factor. The graph shows that there is an inverse relationship between the coefficient of the white factor and the weight of the Eumelanin factor. The equation of the graph is given by:

$$C_W = 1.662 W_{EU}^2 - 3.3983 W_{EU} + 1.7732, \qquad \text{(Equation 6)}$$

where $C_W$ is the coefficient of the white factor and $W_{EU}$ is the weight of the Eumelanin factor. It will be appreciated by those skilled in the art, that equation 6 can be recalculated by performing limited experiments using another bleaching substance on a sample of hairs. It should be noted that only the constants of equation 6 change with different bleaching substances. It is seen from equation 6 that the final coefficient of the white factor is calculated from the final weight of Eumelanin after bleaching. Once the final coefficient of the white factor after bleaching has been calculated, the final coefficients of the other factors are calculated using the basic algebra and the following equations:

$$W_{EU-F} = \frac{C_{EU-F}}{C_{EU-F} + C_{PH-F} + C_{W-F} + C_{ER-F}}, \qquad \text{(Equation 7)}$$

-continued $$W_{PH-F} = \frac{C_{PH-F}}{C_{EU-F} + C_{PH-F} + C_{W-F} + C_{ER-F}},$$ (Equation 8)

$$W_{W-F} = \frac{C_{W-F}}{C_{EU-F} + C_{PH-F} + C_{W-F} + C_{ER-F}},$$ (Equation 9)

where $W_{EU-F}$ is the final weight of the Eumelanin factor, $W_{PH-F}$ is the final weight of the Pheomelanin factor, $W_{W-F}$ is the final weight of the white factor, $C_{EU-F}$ is the final coefficient of the Eumelanin factor, $C_{PH-F}$ is the final coefficient of the Pheomelanin factor, $C_{W-F}$ is the final coefficient of the white factor and $C_{ER-F}$ is the final coefficient of the error factor. It should be noted that the coefficient of the error factor is not effected by bleaching or dyeing and therefore the known coefficient of the error factor for the apparatus concerned can be used in equations 7, 8 and 9. Alternatively, if three factor analysis is used the error factor can be ignored.

It should be noted that the above equations are used to calculate the effects of bleaching on the reflectance spectrum of hair when the hair is of normal quality, that is the hair cuticle is not tightly closed and not abnormally open. However, when the cuticle of the hair is open more than average or closed more than average, the hair is bleached quicker or slower, respectively, and therefore requires less or more bleaching time, respectively. Therefore, the above formulas need to be adjusted for any change in bleaching time due to the condition of the cuticle. It is estimated that the bleaching time needs to be adjusted between 5% and 50% due to the status of the cuticle. Experienced hairdressers are skilled in the art of detecting inferior quality hair, which is associated with the status of the cuticle.

By way of introduction, dyeing hair generally alters the weights of the natural hair factors as well as adding a new factor of the dye itself. The final weight of the dye is a function of the sum of the changes of the weights of the natural hair factors, as shown by the following equation:

$$W_{DYE-F} = f(\Delta W_{EU} + \Delta W_{PH} + \Delta W_W + \Delta W_{ER})$$ (Equation 10), where $W_{DYE-F}$ is the final weight of the dye, $\Delta W_{EU}$ is the change in the Eumelanin factor due to dyeing, $\Delta W_{PH}$ is the change in the Pheomelanin factor due to dyeing, $\Delta W_W$ is the change in the white factor due to dyeing and $\Delta W_{ER}$ is the change in the error factor due to dyeing. For the sake of clarification, $\Delta W_{EU}$ is equal to the final weight of the Eumelanin factor less the initial weight of the Eumelanin factor. Similarly, all the changes in weights and coefficients of the various factors are defined as the final value less the initial value of the weight or coefficient of the factor concerned. It should be noted that the effect of the change in the weight of the error factor on the weight of the dye is generally negligible and can be ignored. Moreover, if three-factor analysis is used the error factor is also ignored. The weight difference of the Eumelanin factor is correlated with the change in the coefficient of the white factor divided by the initial weight of the weight factor among the background. This is illustrated by the following equation:

$$\Delta W_{EU} = f\left(\frac{\Delta C_W}{W_{W-i-B}}\right),$$ (Equation 11)

where $\Delta C_W$ is the change in the coefficient of the white factor due to dyeing and $W_{W-i-B}$ is the initial weight of the white factor among the background.

Additionally the final weight of the dye factor is highly correlated with the final coefficient of the dye factor. This is illustrated by the following equation:

$$C_{DYE} = f(W_{DYE-F})$$ (Equation 12), where $C_{DYE}$ is the final coefficient of the dye factor and $W_{DYE-F}$ is the final weight of the dye factor.

Additionally, the following relationships are valid, given by the following equations:

$$\Delta W_{PH} = f((1 - W_{EU-i}) \times W_{PH-i-B})$$ (Equation 13), $$\Delta C_W = f((1 - W_{EU-i}) \times W_{W-i-B})$$ (Equation 14), where $W_{EU-i}$ is the initial weight of the Eumelanin factor, $W_{PH-i-B}$ is the initial weight of the Pheomelanin factor among the background. Therefore, it can be seen that limited experimentation for each dye or a combination of dyes can be performed using a number of hair samples to determine the functions of equations 10 to 14 for each dye or combination of dyes. The limited experimentation involves calculating the coefficients and weights of all the factors before and after dyeing. The results are then plotted on suitable graphs and the functions of equations 10 to 14 are determined by the equations of the slope of the graphs. For example, the function of equation 10 is determined by plotting a graph of $W_{DYE-F}$ against $(\Delta W_{EU} + \Delta W_{PH} + \Delta W_W + \Delta W_{ER})$. The determined equations, for a specific dye, or combination of dyes are used to predict the change on the reflectance spectrum by applying the dye or combination of dyes, as will be explained with reference to FIG. 6. The hair samples should be from natural unbleached hairs. Hair samples from at least five individuals should be used. Each sample of hair from the same individual should be divided into several smaller samples so that each smaller sample can be bleached for a different duration of time. Each sample is then dyed. This procedure is repeated for each individual. The samples used should be chosen such that, the samples give a large spread over the range of possible natural hair colors (from bright hair to dark hair). The total number of points on each graph should be at least 15. It is advisable to apply the dye according to the manufacturer instructions using the correct concentrations and waiting times. If the manufacturer instructions are not followed, the dye needs to be applied consistently to ensure that results obtained are meaningful. When a combination of dyes is used the proportions of each dye needs to be carefully maintained.

The factor of the dye or combination of dyes is determined by two methods. The first method involves dyeing white hair with the chosen dye or combination of dyes. A reflectance spectrum of the dye or combination of dyes is measured and factor analysis is performed to identify the new factor associated with the chosen dye or combination of dyes. White hair is preferred as the coefficients of the Eumelanin and Pheomelanin factors are very small and the factor analysis is quicker. The second method includes placing a thick dried droplet of dye or combination of dyes on window 18 of reflectance spectrum measurement system 10 (FIG. 1). The reflectance spectrum of the thick droplet of dye or combination of dyes only contains the contribution of the factor of the chosen dye or combination of dyes and therefore the factor of the dye or combination of dyes is easily identified.

By way of a non-limiting example, experiments were performed using the WELLA KOLESTON 305/0 Light- Brown dye. This dye is produced by Wella AG, Berliner Allee 65, 64274 Darmstadt, Germany. The dye was applied in accordance with the manufacturer instructions. The color tube was packaged with an oxygen cream. The entire contents of the color tube and oxygen cream were mixed together to form the dye. The following equations, based on equations 10 to 14, are valid for the abovementioned dye:

$$W_{DYE-F} = -0.3867(\Delta W_{EU} + \Delta W_{PH} + \Delta W_W + \Delta W_{ER})^2 + 1.0139(\Delta W_{EU} + \Delta W_{PH} + \Delta W_W + \Delta W_{ER}) + 0.0069, \quad \text{(Equation 15)}$$

$$\Delta W_{EU} = -0.2687\left(\frac{\Delta C_W}{W_{W-i-B}}\right) + 0.4013, \quad \text{(Equation 16)}$$

$$C_{DYE} = 5.7757(W_{DYE-F})^2 - 0.519(W_{DYE-F}) + 0.1262 \quad \text{(Equation 17)},$$

$$\Delta W_{PH} = 1.1689((1-W_{EU-i}) \times W_{PH-i-B}) - 0.0688 \quad \text{(Equation 18)},$$

$$\Delta C_W = 2.6671((1-W_{EU-i}) \times W_{W-i-B}) - 0.1573 \quad \text{(Equation 19)}.$$

It should be noted that other dyes have equations, which have a similar form to equations 14 to 19, but with different constants.

Figure 6:
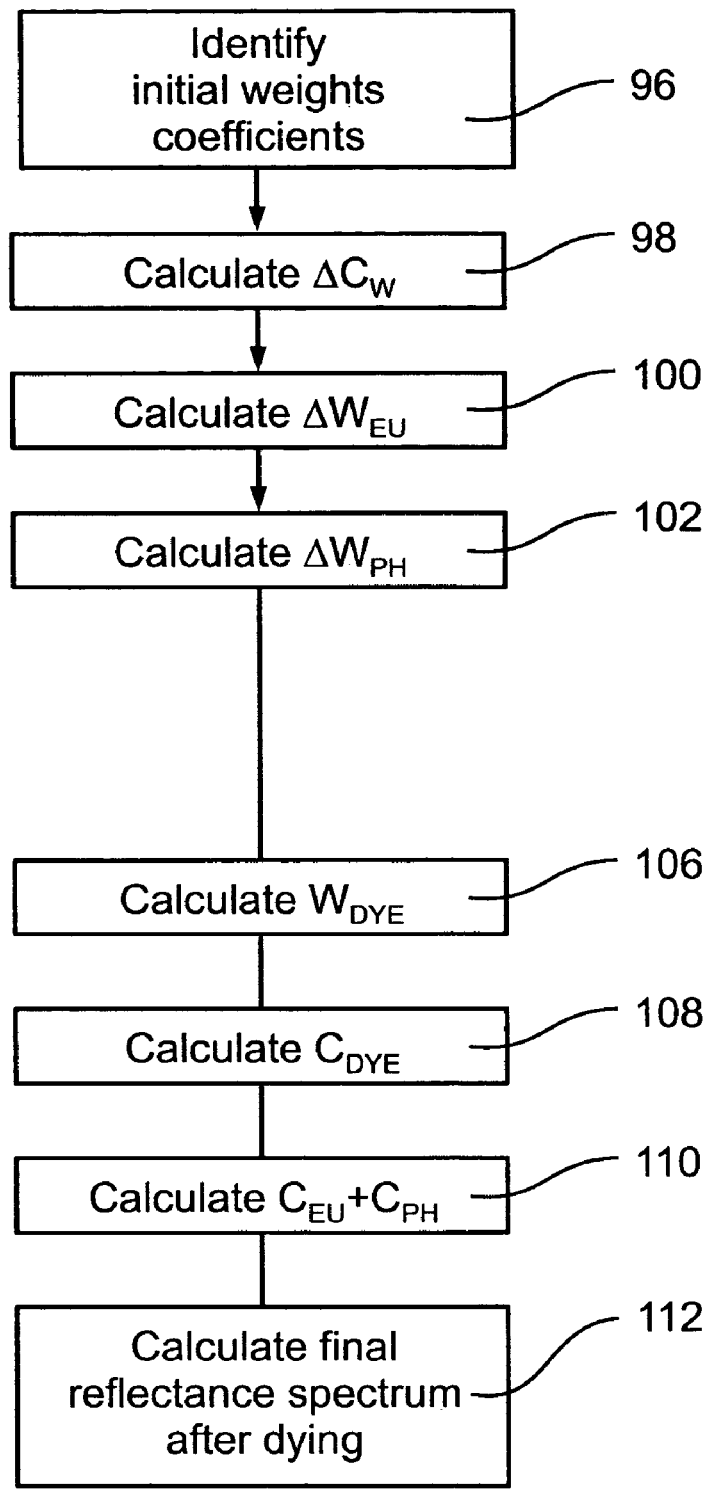
FIG. 6 is a flow chart of the steps involved in determining the effects of dyeing on the reflectance spectrum of hair.

Reference is now made to FIG. 6, which is a flow chart of the steps involved in determining the effects of dyeing on the reflectance spectrum of hair. First, if bleaching is to be performed the final weights after bleaching are used as the initial weights before dyeing. If bleaching is not performed or actual bleaching has already been performed on the customer's hair, a new reflectance spectrum is measured and the coefficients and weights of the new reflectance spectrum are analyzed and calculated, respectively (block 96). Second, final coefficient of the white factor is calculated using equation 14 (block 98). Third, the final weight of the Eumelanin factor, after dyeing, is calculated using equation 11 (block 100). Fourth, the final weight of the Pheomelanin factor, after dyeing, is calculated using equation 13 (block 102). Fifth, the final weight of the dye is calculated using equation 10 (block 106). Sixth, the final coefficient of the dye is calculated using equation 12 (block 108). Seventh, the final coefficients of the Eumelanin and Pheomelanin factors are calculated using algebra and equations 7 to 9 (block 110). Finally, the final reflectance spectrum after dyeing is determined by summing the product of each factor with the factor's final coefficient after dyeing (block 112).

By way of introduction, when there is a very high resemblance between the spectrum of the chosen dye and one of the natural hair factors, the method described with reference to FIG. 6 becomes impractical. This is because the very high resemblance between the dye and one of the natural hair factors requires a very high resolution during the searching process of the curve fitting program to be enable identification of the coefficients of the dye factor and the closely matched natural hair factor. Therefore, another method is needed to predict the effect on the reflectance spectrum of hair due to dyeing, where the dye factor has a very close resemblance to one of the natural hair factors.

One method is to merge the final weight of the dye factor and the closest natural hair factor. By way of example, when the dye factor is very close to the Pheomelanin factor, the following relationship is valid:

$$W_{DYE+PH} = f(W_{EU-i}) \quad \text{(Equation 20)},$$

where $W_{DYE+PH}$ is the final weight of the merged dye and Pheomelanin factor after dyeing and $W_{EU-i}$ is the initial weight of the Eumelanin factor.

Additionally, the following relationships are valid:

$$\Delta W_W = f((1-W_{EU-i}) \times W_{W-i-B}) \quad \text{(Equation 21)},$$

$$\Delta W_{EU} = f\left(\frac{\Delta W_W}{W_{W-i-B}}\right), \quad \text{(Equation 22)}$$

$$C_W = f(W_{W-F}), \quad \text{(Equation 23)}$$

where $\Delta W_W$ is the change in the weight of the white factor due to dyeing, $W_{W-i-B}$ is the initial weight of the white factor among the background, $\Delta W_{EU}$ is the change in the weight of the Eumelanin factor due to dyeing, $C_W$ is the final coefficient of the white factor and $W_{W-F}$ is the final weight of the white factor. Therefore, it can be seen that limited experimentation for each dye or combination of dyes can be performed using a number of hair samples to determine the functions of equations 20 to 23 for each dye or combination of dyes, as described above with reference to equations 10 to 14. The limited experimentation involves calculating the coefficients and weights of all the factors before and after dyeing. The results are then plotted on suitable graphs and the functions of equations 20 to 23 are determined by the equations of the slope of the graphs. The determined equations, for a specific dye or combination of dyes, are used to predict the change on the reflectance spectrum by applying the dye or combination of dyes, as will be explained with reference to FIG. 7. It is advisable to apply the dye according to the manufacturer instructions using the correct concentrations and waiting times. If the manufacturer instructions are not followed, the dye needs to be applied consistently to ensure that results obtained are meaningful. When a combination of dyes is used the proportions of each dye needs to be carefully maintained.

By way of a non-limiting example, experiments were performed using the WELLA KOLESTON 307/64 Cherry dye manufactured by Wella AG. This Cherry Dye has a very high resemblance to the Pheomelanin factor. The dye was applied in accordance with the manufacturer instructions. The color tube was packaged with an oxygen cream. The entire contents of the color tube and oxygen cream were mixed together to form the dye. The following equations, based on equations 20 to 23 are valid for the abovementioned dye:

$$W_{CHERRY+PH} = -0.1467(W_{EU-i})^2 - 0.2543(W_{EU-i}) + 0.4336 \quad \text{(Equation 24)},$$

$$\Delta W_W = 0.7232((1-W_{EU-i}) \times W_{W-i-B}) - 0.017 \quad \text{(Equation 25)},$$

$$\Delta W_{EU} = 0.547\left(\frac{\Delta W_W}{W_{W-i-B}}\right) + 0.0378, \quad \text{(Equation 26)}$$

$$C_W = 1.6079(W_{W-F}) - 0.0079 \quad \text{(Equation 27)},$$

where $W_{CHERRY+PH}$ is the final weight of the cherry dye and Pheomelanin factor combined. It should be noted that other dyes have equations, which have a similar form to equations 24 to 27, but with different constants.

Figure 7:
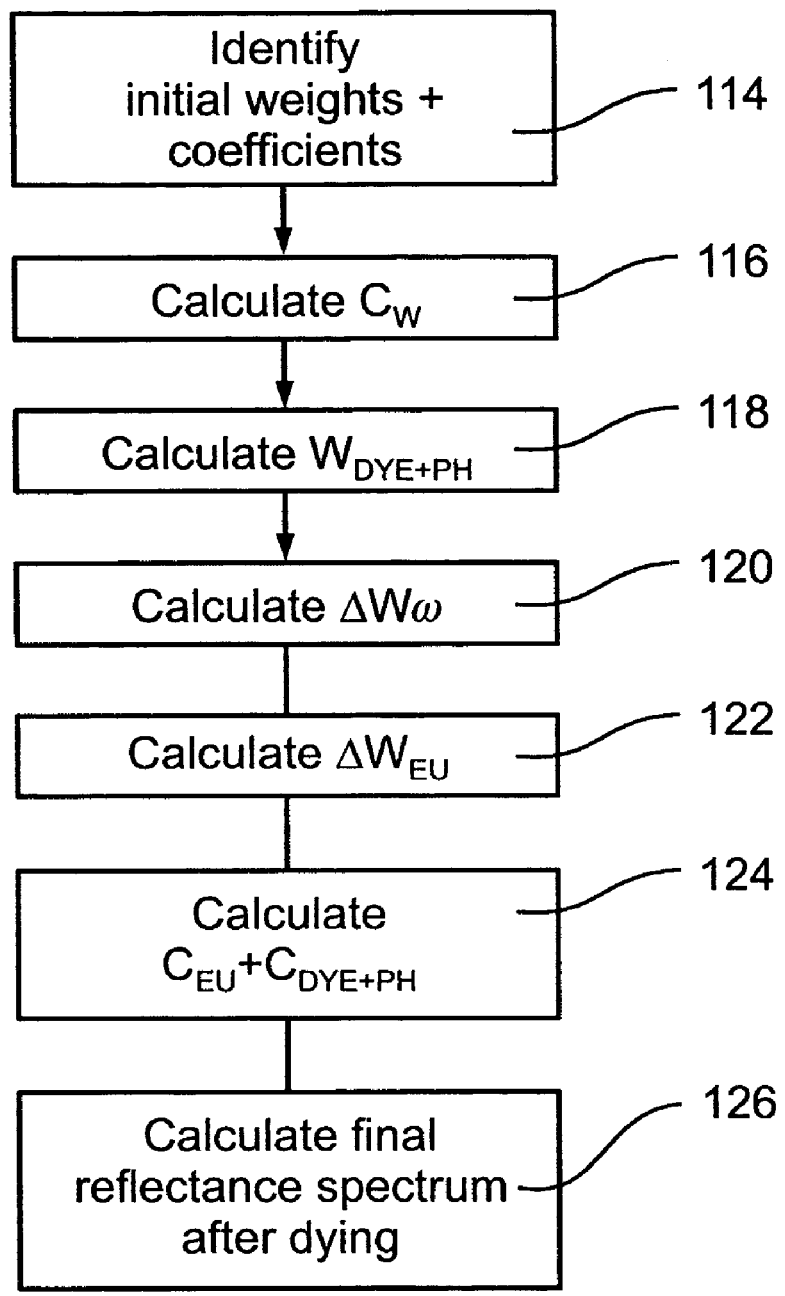
FIG. 7 is a flow chart of the steps involved in determining the effects of dyeing on the reflectance spectrum of hair using a dye having a similar factor to natural factors.

FIG. 7 is a flow chart of the steps involved in determining the effects of dyeing on the reflectance spectrum of hair using a dye having a similar factor to natural factors. First, if bleaching is to be performed the final weights after bleaching are used as the initial weights before dyeing. If bleaching is not performed or actual bleaching has already been performed on the customer's hair, a new reflectance spectrum is measured and the coefficients and weights of the new reflectance spectrum are analyzed and calculated, respectively (block 114). Second, final coefficient of the white factor is calculated using equation 23 (block 116). Third, the final weight of the merged dye and Pheomelanin factor is calculated using equation 20 (block 118). Fourth, the final weight of the white factor, after dyeing, is calculated using equation 21 (block 120). Fifth, the final weight of the Eumelanin factor, after dyeing, is calculated using equation 22 (block 122). Sixth, the final coefficients of the Eumelanin and merged dye and Pheomelanin factors are calculated using algebra and equations 28 to 30, below (block 124).

$$W_{EU-F} = \frac{C_{EU-F}}{C_{EU-F} + C_{DYE+PH-F} + C_{W-F} + C_{ER-F}}, \quad \text{(Equation 28)}$$

$$W_{H-F} = \frac{C_{PH-F}}{C_{EU-F} + C_{DYE+PH-F} + C_{W-F} + C_{ER-F}}, \quad \text{(Equation 29)}$$

$$W_{W-F} = \frac{C_{W-F}}{C_{EU-F} + C_{DYE+PH-F} + C_{W-F} + C_{ER-F}}, \quad \text{(Equation 30)}$$

where, $W_{EU-F}$ is the final weight of the Eumelanin factor, $W_{DYE+PH-F}$ is the final weight of the merged dye and Pheomelanin factor, $W_{W-F}$ is the final weight of the white factor, $C_{EU-F}$ is the final coefficient of the Eumelanin factor, $C_{DYE+PH-F}$ is the final coefficient of the merged dye and Pheomelanin factor, $C_{W-F}$ is the final coefficient of the white factor and $C_{ER-F}$ is the final coefficient of the error factor. Finally, the final reflectance spectrum after dyeing is determined by summing the product of each factor with the factor's final coefficient after dyeing (block 126).

If the factor of the chosen dye has a similar factor to the Eumelanin factor, then the final reflectance spectrum after dyeing will be very similar to the Eumelanin factor.

Natural hair factor dyes, dyes that have a very high correlation with the natural hair factors of Eumelanin and Pheomelanin, are created by mixing existing dyes so that the combination of dyes exhibits a reflectance spectrum which is very close to the Eumelanin or Pheomelanin factor, respectively. Natural hair factor dyes are used when the desired final color is a natural hair color. Limited experiments are performed with different proportions of the natural hair factor dyes to determine the dyeing equations for these different proportions. The computer calculates a hair treatment by performing iterative calculations using the equations for the different proportions of the natural hair dyes. It is advantageous to use natural hair factor dyes, as a new factor is not introduced into the hair by the dyeing process. Therefore, the computer iteration process is quicker. Then the natural hair factor dyes can be used to dye hair to a natural hair color.

Figure 8A:
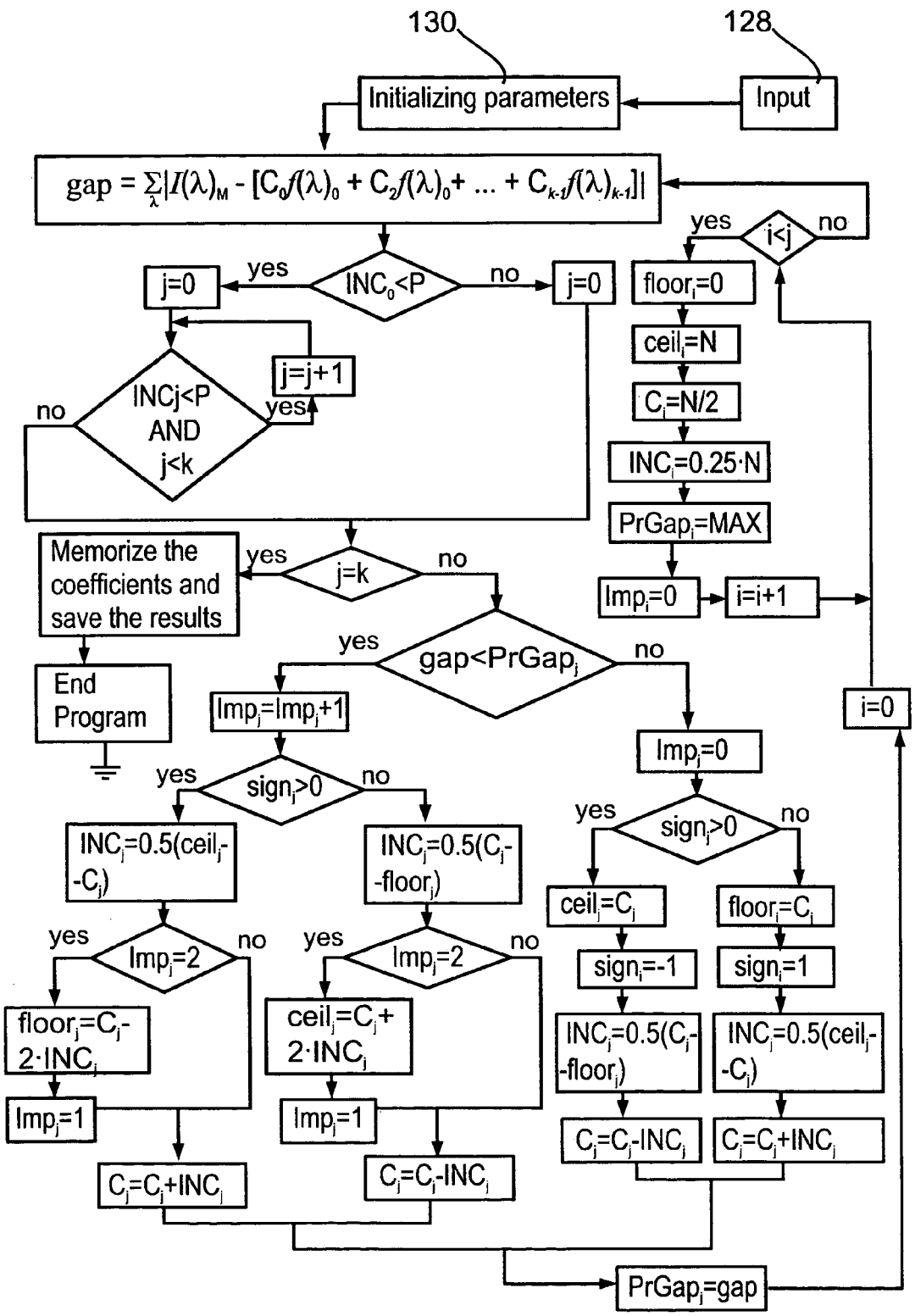
FIG. 8a is a flow chart to enable a programmer to write a program to perform coefficient analysis.
Figure 8B:
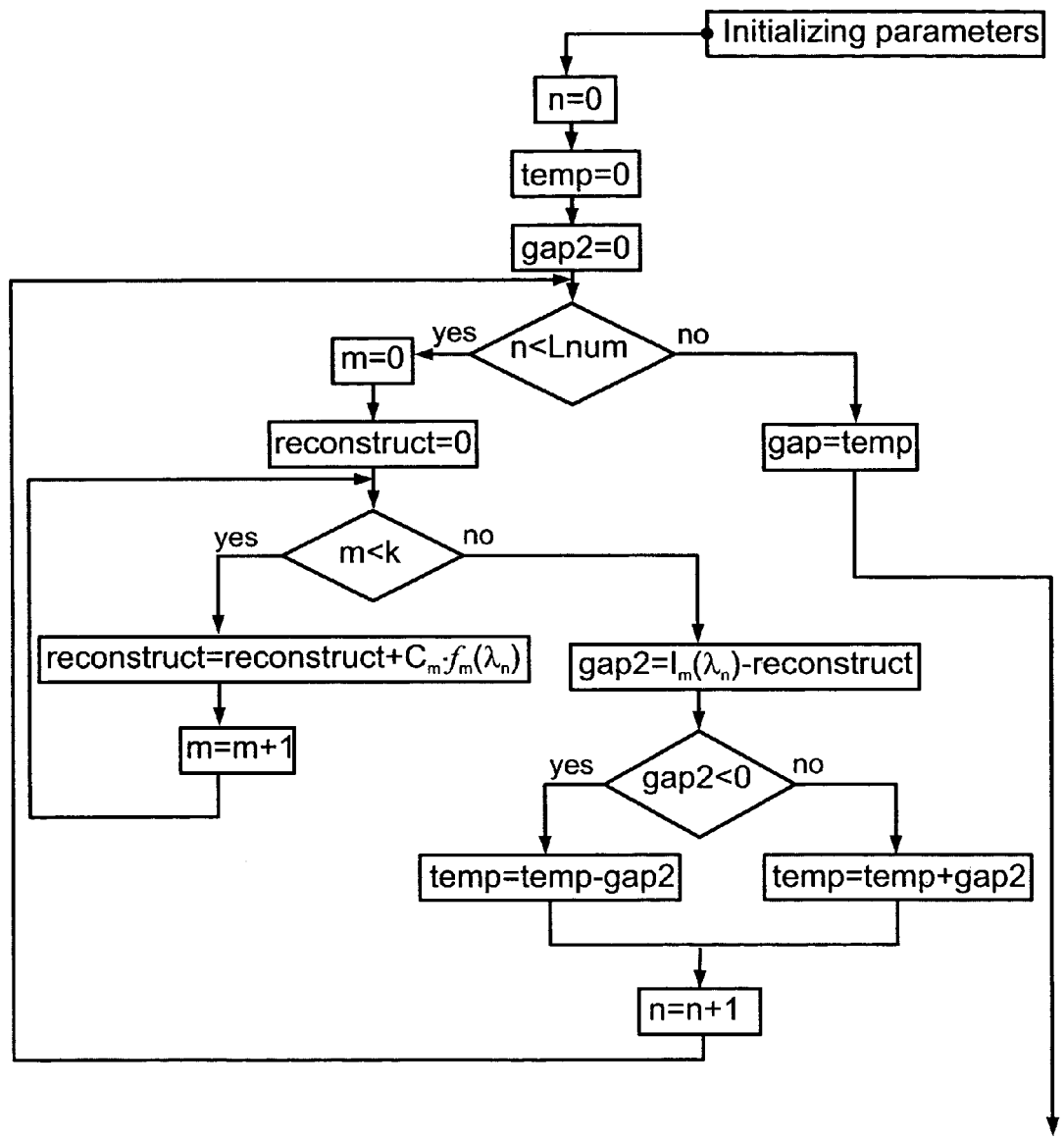

Reference is flow made to FIG. 8*a*, which is a flow chart of an algorithm to enable a programmer to write a program to perform coefficient analysis. Reference is also made to FIG. 8*b*, which is a detailed flow chart of part of the process shown in FIG. 8*a* given by the term:

$$\text{gap} = \sum_{\lambda} |I(\lambda)_M - [C_0 f(\lambda)_0 + C_1 f(\lambda)_1 + \ldots + C_{k-1} f(\lambda)_{k-1}]|$$

The algorithm extracts the appropriate coefficients of the factors by performing iterations until the coefficients produce a reflectance spectrum, which is as close to the measured reflectance spectrum as possible. The algorithm assumes that the computer program is written in Borland c version 5.01. The following parameters used in the flowchart are defined below:

k is the number of factors (a constant).

j is an integer parameter with values from 0 to k−1.

i is an integer parameter with values from 0 to k−1.

n, m are variable integers.

temp, gap2, reconstruct are variables.

$\lambda_n$ is the $n^{th}$ wavelength in an array of wavelengths, the array having Lnum members, n being the index of the wavelength within the array (a constant).

Lnum is the number of wavelengths (a constant). Therefore, n=0,1, . . . ,(Lnum−1).

$I(\lambda)_M$ is the relative reflectance of a wavelength within an array of wavelengths, the array having Lnum cells for the Lnum wavelengths in the array (constant values).

$C_j$ is the coefficient of the $j^{th}$ factor. There are k parameters of this type, which are iterated during the calculations until all k parameters of $INC_j$ (defined below) are smaller than P (defined below).

$f(\lambda)_j$ represents the spectrum of $j^{th}$ factor and is an array of Lnum cells.

gap is a parameter that receives the summation of absolute differences from the curve of measurement to the curve of reconstruction. The curve of reconstruction is represented by the term: $C_1 \cdot f(\lambda)_1 + C_2 \cdot f(\lambda)_2 + \ldots + C_k \cdot f(\lambda)_k$ $INC_j$ is a parameter that contains the incremental change in the coefficient of the $j^{th}$ factor used in the last iteration.

P is a constant parameter of precision. Its value is set before starting the process of iterations among the coefficients (this setting can be a part of the program).

$PrGap_j$ contains the last value of the parameter gap of when the coefficient of the $j^{th}$ factor was iterated.

MAX is a constant number that represent a very high value that the parameter gap cannot exceed.

$floor_j$ is the lowest value that the coefficient of the $j^{th}$ factor can receive at each iteration (variable).

$ceil_j$ is the highest value that the coefficient of the $j^{th}$ factor can receive at each iteration (variable).

N is a constant parameter that represents the maximum magnitude that any coefficient can possibly have. The parameter $ceil_j$ cannot exceed the value of this parameter.

$Imp_j$ tracks the iteration process. It is an integer parameter that counts how many successive fitting improvements have occurred for the coefficient of the $j^{th}$ factor. The indication of improvement is a reduction in the value of $PrGap_j$.

$sign_j$ is an integer parameter that indicates whether the coefficient of the $j^{th}$ factor is being iterated by increasing it or decreasing it.

The flowchart begins with a block 128. At this point, the arrays of the spectrums of the factors and the measured reflectance spectrum are loaded from the database. Also at this point the array of the wavelengths, in a sequence of numbers from the first wavelength to last wavelength in the range, are loaded. The arrays of the spectrums are configured to contain an identical number of cells as the array of the wavelengths. At block 130 the parameter are initialized. The following parameters are initialized with the following values:

$floor_0=0$, $floor_1=0$, . . . , $floor_{k-1}=0$

N is the maximum value a coefficient can possibly have (as described above). The maximum value of the measured reflectance spectrum is divided by the maximum value of the factor with the lowest maximum value giving N minus 1.

$ceil_0=N$, $ceil_1=N$, . . . , $ceil_{k-1}=N$ $C_1=N/2, C_2=N/2, \ldots, C_k=N/2$ $$INC_0 = \frac{N}{4}, INC_1 = \frac{N}{4}, \ldots, INC_{k-1} = \frac{N}{4}$$

$Imp_0=0, Imp_1=0, \ldots, Imp_k 32\ 0$
MAX=999999999999, being much bigger than N.
$PrGap_0=MAX, PrGap_1=MAX, \ldots, PrGap_{k-1}=MAX$
j=0

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art which would occur to persons skilled in the art upon reading the foregoing description.

What is claimed is:

1. A method to change the color of hair, comprising the steps of:
    (a) producing a reflectance spectrum of a sample of the hair;
    (b) sampling said reflectance spectrum at data points therealong; and
    (c) using said data points, analyzing a contribution of a plurality of factors to said spectrum, wherein each of said factors has a unique respective factor spectrum.

2. The method of claim 1, wherein said at least two of said factors are natural hair factors, one of said factors relating to Eumelanin, another of said factors relating to Pheomelanin.

3. The method of claim 1, further comprising the step of:
    (d) calculating a new reflectance spectrum of the hair based on a hypothetical hair treatment for the hair.

4. The method of claim 3, wherein said step of calculating is based on a new contribution of said factors after said hypothetical hair treatment.

5. The method of claim 1, further comprising the step of:
    (e) determining a treatment for the hair that gives said hair a desired resultant spectrum.

6. A method to change the color of hair, comprising the steps of:
    (a) producing an initial reflectance spectrum of a sample of the hair;
    (b) sampling said initial reflectance spectrum at data points therealong; and
    (c) calculating a new spectrum of the hair as a function of said sampled initial spectrum and of a spectrum of hypothetical hair treatment for the hair.

7. The method of claim 6, wherein said function is non linear.

8. A method to change the color of hair, comprising the steps of:
    (a) producing an initial reflectance spectrum of a sample of the hair;
    (b) sampling said initial reflectance spectrum at data points therealong; and
    (c) determining a treatment for the hair as a function of said sampled initial spectrum and of desired spectrum of the hair.

9. The method of claim 8, wherein said function is a non linear function.

10. A method to create a natural hair factor dye having a factor which is substantially the same as a natural hair factor, the natural hair factor relating to one of Eumelanin and Pheomelanin, the method comprising the steps of:
    (a) mixing a plurality of dyes to create a mixed dye; and
    (b) measuring a reflectance spectrum of said mixed dye, and
    (c) iterating said mixing and said measuring until said spectrum is substantially identical to a spectrum of the natural hair factor.

11. A hair color changing system, comprising a processor configured for:
    (a) producing a reflectance spectrum of a sample of hair;
    (b) sampling said reflectance spectrum at data points therealong; and
    (c) using said data points, analyzing a contribution of a plurality of factors to said spectrum, wherein each of said factors has a unique respective factor spectrum.

12. The system of claim 11, wherein said at least two of said factors are natural hair factors, one of said factors relating to Eumelanin, another of said factors relating to Pheomelanin.

13. The system of claim 11, wherein said processor is further configured for calculating a new reflectance spectrum of said hair based on a hypothetical hair treatment for said hair.

14. The system of claim 13, wherein said calculating is based on a new contribution of said factors after said hypothetical hair treatment.

15. The system of claim 11, wherein said processor is further configured for determining a treatment for said hair that gives said hair a desired resultant spectrum.

16. A hair color changing system, comprising a processor configured for:
    (a) producing an initial reflectance spectrum of a sample of hair;
    (b) sampling said initial reflectance spectrum at data points therealong; and
    (c) calculating a new spectrum of said hair as a function of said sampled initial spectrum and of a spectrum of a hypothetical hair treatment for the hair.

17. The system of claim 16, wherein said function is non-linear.

18. A hair color changing system, comprising a processor configured for:
    (a) producing an initial reflectance spectrum of a sample of the hair;
    (b) sampling said initial reflectance spectrum at data points therealong; and
    (c) determining a treatment for the hair as a function of said sampled initial spectrum and of a desired spectrum of the hair.

19. The system of claim 18, wherein said function is a non-linear function.

* * * * *